United States Patent [19]
Neal

[11] Patent Number: 5,695,453
[45] Date of Patent: Dec. 9, 1997

[54] LIMB IMMOBILIZER HAVING REINFORCING WIRE MEMBERS EMBEDDED THERIN

[75] Inventor: Charles O. Neal, Knoxville, Tenn.

[73] Assignee: DeRoyal Industries, Inc., Powell, Tenn.

[21] Appl. No.: 577,971

[22] Filed: Dec. 22, 1995

[51] Int. Cl.⁶ .................................................. A61F 5/00
[52] U.S. Cl. .................... 602/6; 602/21; 602/23; 602/64; 602/46
[58] Field of Search ................ 602/6, 9, 20–21, 602/23, 14, 27, 61–65, 46

[56] References Cited

U.S. PATENT DOCUMENTS

| | | | |
|---|---|---|---|
| 937,769 | 10/1909 | Collis | 602/64 |
| 1,070,869 | 8/1913 | Alexander | 602/5 |
| 2,933,083 | 4/1960 | Kozdas | 602/6 |
| 3,232,289 | 2/1966 | Zimmerman | 602/6 |
| 3,804,084 | 4/1974 | Lehman | 602/62 X |
| 3,942,522 | 3/1976 | Wilson | 602/14 X |
| 4,013,070 | 3/1977 | Harroff | 602/27 X |
| 4,161,175 | 7/1979 | Bentele | 602/6 |
| 4,961,418 | 10/1990 | McLaurin-Smith | 602/21 |
| 5,160,314 | 11/1992 | Peters | 602/64 X |
| 5,307,521 | 5/1994 | Davis | 602/5 X |
| 5,356,371 | 10/1994 | Hubbard | 602/6 X |

*Primary Examiner*—Linda C. Dvorak
*Attorney, Agent, or Firm*—Paul E. Hodges, P.C.

[57] ABSTRACT

A limb immobilizer including a soft foam body member in which there is embedded a system of reinforcing and stabilizing wire members, the body member being amenable to being readily conformed to the shape and size of a limb, and strapping means for securing the immobilizer in place on the limb. Opening through the thickness of the body member facilitate the application of the body member to a limb. A novel body member for a limb immobilizer is disclosed.

13 Claims, 3 Drawing Sheets

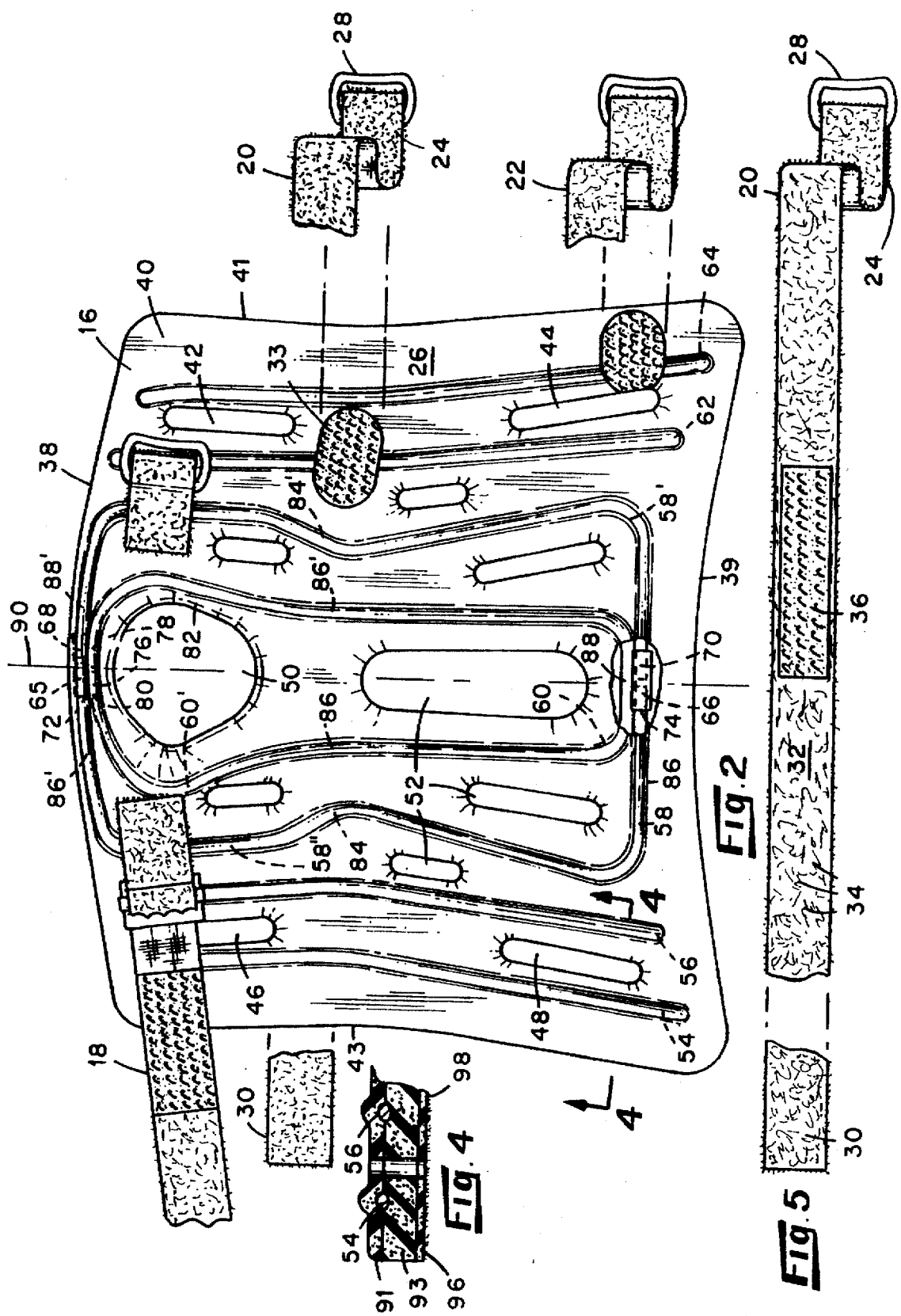

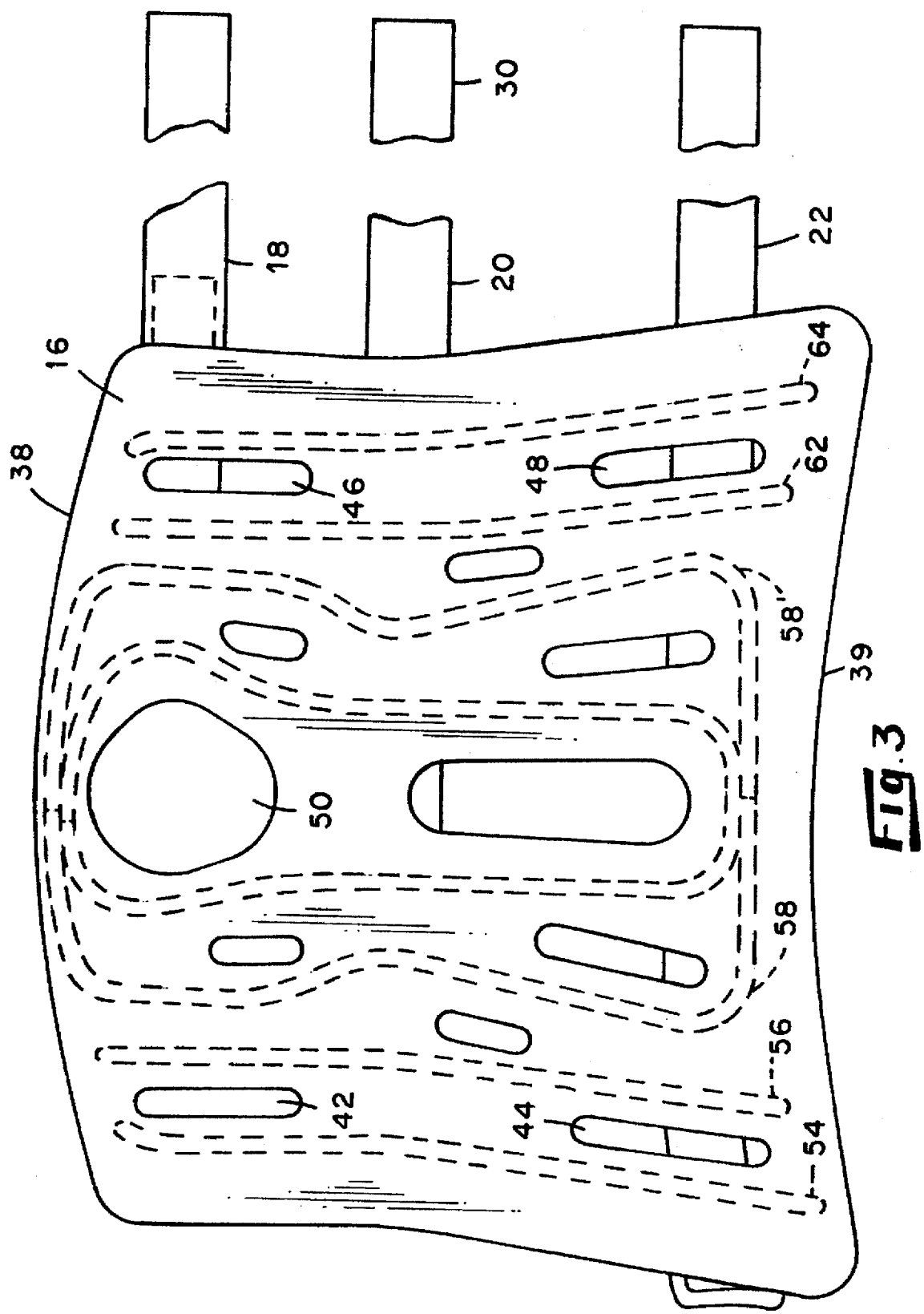

5,695,453

1

LIMB IMMOBILIZER HAVING REINFORCING WIRE MEMBERS EMBEDDED THERIN

FIELD OF INVENTION

This invention relates to medical devices useful in the immobilization of a limb, particularly the extremity of a limb such as a wrist or ankle.

BACKGROUND OF INVENTION

Treatment of a sprain, strain or break in the area of a wrist or ankle, i.e. in the area of the extremity of a limb, may take the form of a cast or a removable immobilizer. Removable immobilizers are commonly used where the injury involves a "stable" injury, that is there is no displacement of a broken bone or the displacement, if any, is such as can be rectified without the necessity of casting. "Unstable" injuries involving displace broken bones commonly are placed in a cast. The present invention is directed to an immobilizer which may be used with stable injuries or with unstable injuries which have been treated with a cast, but have healed to the extent that the cast may be removed, but a degree of immobilization and protection of the injured limb is desired.

Limb immobilizers commonly comprise some form of relatively soft covering for the injured area, this covering being contoured to only the approximate size and shape of a wrist or ankle, for example, and made available in sizes. Contouring of the covering is commonly by means of rigid plastic shells or by means of a plurality of metal stays that are shaped to define the contour of the immobilizer. Adjustment of the contour of these prior immobilizers by a medical worker is usually not possible due to the rigidity of the plastic shell or due to the type of material from which the stay of made, or the extreme resistance of the stay to its being reshaped in the field. This situation has resulted in the necessity of inventorying of several sizes of immobilizers of a given type in order to have available an immobilizer which will fit a particular patient.

Universally sized immobilizers have been proposed in which the covering is pliable and readily conformable to the contour of the wrist or ankle. This covering is placed on the injured limb and then secured in position by means of lacing or multiple straps that are positioned strategically on the covering to effect immobilizaton of the limb extremity. In this type immobilizer, the degree of immobilization is wholly dependent upon the placement and effectiveness of the lacing or strapping.

In certain immobilizers of the prior art, metal stays are inserted into pockets disposed on the outer surface of a pliable conformable covering for the injured area. Certain of these stays have been made of a material which permits some degree of recontouring of the stay in the field. These products, however, suffer from the fact that the stays can not be recontoured after the covering and accompanying stays have been applied to the injured area. Therefore, to ensure the desired close conformity of the immobilizer to the contour of the injured limb, it most often requires that the stays be initially bent (contoured) to an estimated degree. Thereafter, the immobilizer if then placed on the injured limb to check the degree of conformity. If the conformity is not proper, the immobilizer must be removed and further bending of the stays done. Again this readjusted immobilizer must be placed on the injured limb to check its conformity. This procedure may often require repeated adjustments before the immobilizer is properly fitted.

It is therefore an object of the present invention to provide an immobilizer for a limb, particularly the extremity of a limb.

2

It is another object of the present invention to provide an immobilizer for a limb wherein the immobilizer is readily conformable to the contour of the injured area of the limb as the immobilizer is being positioned about the limb, and, without removal of the immobilizer from the limb, can be further contoured to the shape and size of the injured area of the limb.

It is another object of the present invention to provide an immobilizer of the type described wherein the immobilizer may be fitted to a range of limb sizes and contours.

It is another object of the present invention to provide an immobilizer of the type described wherein the immobilizer is readily positionable about the injured limb.

Other objects and advantages of the invention will be recognized from the description and claims contained herein, including the drawings in which:

FIG. 2 is a top plan view of a sheet of material from which the immobilizer depicted in FIG. 1 may be formed and including a cutaway view of a portion of the sheet;

FIG. 3 is a bottom plan view of the sheet of material depicted in FIG. 2;

FIG. 4 is a sectional view of the sheet depicted in FIG. 2 and taken generally along the line 4—4 of FIG. 2; and FIG. 5 is a representation of one embodiment of a strap as employed in the present invention.

SUMMARY OF INVENTION

Figure 1:
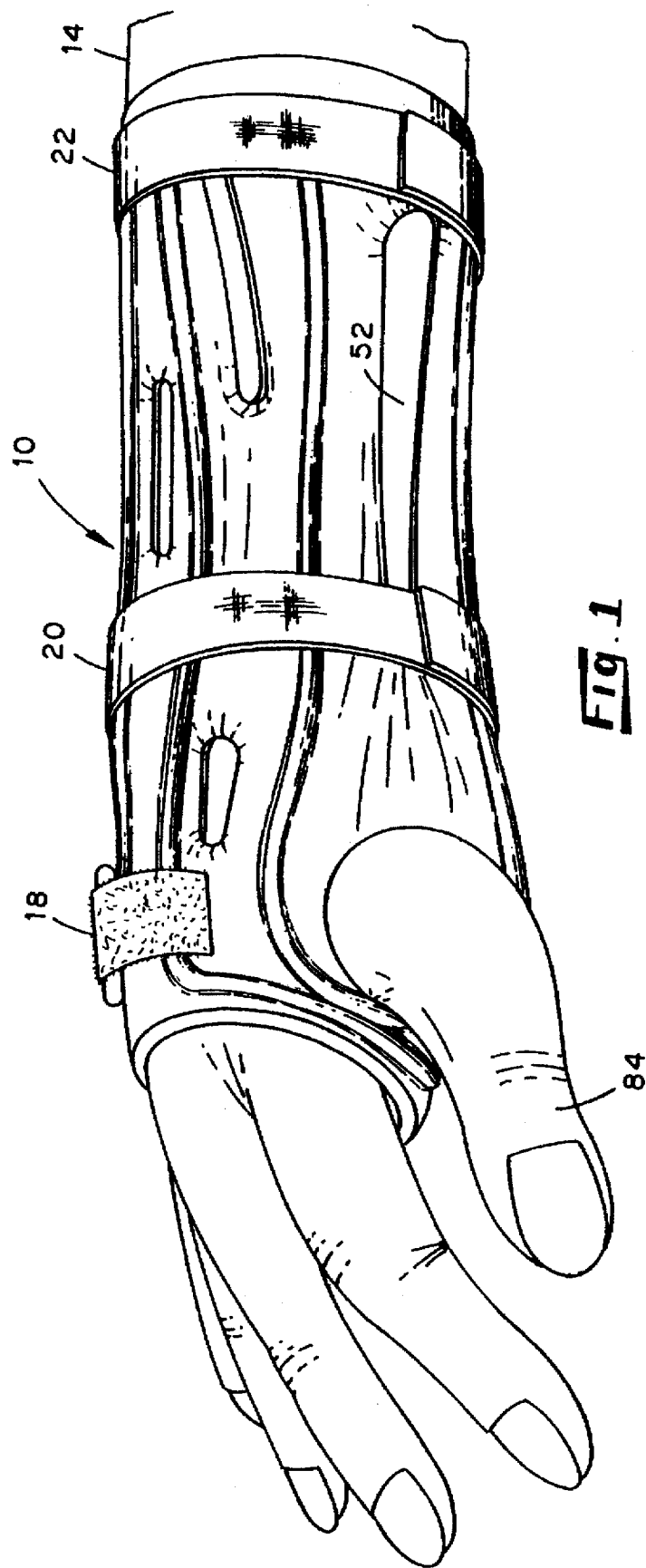
FIG. 1 is a perspective view of an immobilizer as applied to a patient's wrist and which embodies various of the features of the present invention.

In accordance with the present invention there is provided an immobilizer particularly useful for the extremity of a limb, such as the wrist or ankle, and comprising a flat sheet of foam material of a size and shape suitable to be formed about the limb extremity. In a preferred embodiment of the invention, this sheet is of a soft foam material having an outer skin which is smooth, pliable and soil-resistant. Embedded within the sheet is a system of reinforcing and stabilizing wire members, the wire members being malleable and therefore capable of being readily formed by an attending medical worker into close conformity with the shape of the extremity. The soft foam material further serves as a cushioning material between the reinforcing wire members and the extremity and as a shock absorber against blows to the immobilizer during normal use of the extremity after the immobilizer has been applied. Strap means are provided to releasably hold the foam sheet in its conforming position about the extremity. In accordance with one aspect of the invention, the sheet is provided with a plurality of elongated openings through the thickness thereof and being located at spaced apart locations on the sheet. In a preferred embodiment, at least one such elongated opening is provided along one side edge of the sheet and at least one such elongated opening is provided along the opposite side edge of the sheet such that these openings are adjacent one another when the sheet is wrapped about the extremity with the side edges adjacent one another. In this position, these openings serve as "finger holes" into which the medical worker may insert their fingers or thumbs. With the fingers and thumbs of the health worker in opposing adjacent ones of the openings, pinching together of the fingers and thumbs causes the side edges of the sheet to be drawn toward with other, even to the point of overlapping one another, to urge the sheet into an initial conforming encircling relationship to the extremity. This position of the sheet is readily retained by one hand of the medical worker, leaving their other hand free to readily loosely strap the sheet in position about the extremity. Loose initial strapping is desirable in that it is important that the effective length of each wire of the system of wire members which is oriented along the length of the immobilizer be uninhibited from being bent (i.e. recontoured). Thereupon, the medical worker may use their hands to form the malleable wires that are embedded in the sheet to cause the sheet to more completely conform to the shape and size of the extremity. As the degree of conformity is enhanced, the strapping may be drawn tighter. Once the foam sheet is properly formed to the extremity, the strapping is tightened to firmly secure the immobilizer about the limb to render the foam sheet and its embedded wire system sufficiently rigid to immobilize the extremity.

In accordance with another aspect of the invention, the wire members, once formed to the shape and size of the extremity, serve to maintain the conformity of the soft foam sheet to the extremity. If the immobilizer is fitted and applied when the extremity is swollen, as and when the swelling subsides and the circumference of the extremity is reduced, the contour and sizing of the immobilizer may be reselected. This is accomplished by loosening of the straps and merely repeating the procedure of using the hands to mold the sheet about and to the extremity and then resecuring it in position by the strapping.

As noted, the openings 42, 44, 46, and 48 are designed to receive the thumbs and fingers of a health care worker to aid the pulling together of the side edges 41 and 43 in initial encircling relationship to the limb. This action is effected by pinching the thumbs and fingers together while they are inserted in the openings 42, 44, 46, and 48 (one thumb and finger set being inserted in openings 42 and 46, for example, and another thumb and finger set being inserted in openings 44 and 48). This pinching force can be sufficient to tear the foam sheet in the regions of these openings. To avoid this ill effect, each of the openings 42, 44, 46, and 48 is disposed inwardly of their respective one of adjacent reinforcing wire members 64 and 54. By this means, the pinching force is distributed along the side edges 41 and 43 of the foam sheet to minimize the likelihood of tearing the foam sheet. Further, the distribution of the pinching force along the side edges 41 and 43 of the foam sheet tends to bring the entire length of each side edge of the sheet together more uniformly.

Still further, the several openings through the thickness of the sheet serve to permit the inflow and outflow of air through the openings and into the space between the sheet and the extremity, thereby aiding in cooling of the skin under the immobilizer and in the passage of water outward from the skin. To this end, the inner surface of the sheet adjacent to the skin of the patient, preferably is covered with a layer of soft hydrophilic, preferably fibrous, material which enhances the removal of water from the skin, aids in cooling of the space between the sheet and the limb, and helps prevent irritation of the skin.

DETAILED DESCRIPTION OF THE INVENTION

With reference to FIG. 1, the present invention includes an immobilizer 10 for the extremity of a limb 14. Referring also to FIGS. 2–4, the depicted immobilizer comprises a sheet 16 of soft pliant foam material that defines the body of the immobilizer and is formable in encircling relationship to the extremity. Once in position and properly contoured, the sheet is secured in position by means of a plurality of straps 18, 20 and 22. Each strap is anchored at one of its ends, for example end 24 of strap 20, to the outer surface 26 of the sheet 16. In the depicted embodiment, this end 24 is provided with a ring 28 through which the free end 30 of the strap may be threaded (after being wrapped about the immobilizer on the limb) and then pulled back upon itself such that the free end 30 of the strap may be releasably secured to a length of hook material 31 of a hook and loop-type fastener, which is secured on one surface 33 of the strap at a location intermediate of the ends 24 and 30 of the strap, to firmly secure the strap, hence the sheet about the circumference of the extremity. In one embodiment, each strap has at least one surface 32 of brushed nylon fibers 34, for example, which may be engaged with a length of hook material, such as the length 31 secured to the surface 32 of the strap, such as the well-known Velcro-type releasable fastener. As desired, the end 24 of the strap may be permanently anchored to the sheet or it may be releasably anchored to the sheet using a Velcro-type fastener, the hook material 33 thereof being secured to the outer surface 26 of the foam sheet 16. Whereas a specific embodiment of the straps and their means of fastening to the sheet is described, it is to be understood that other types of strapping may be employed, and using any of several well-known means for securing the straps in their encircling relationship about the sheet on the extremity, such as buckles, snaps, and the like. Also, the straps 18 and 22 may be substantially identical to strap 20 or may comprise different materials and/or means of anchoring of the ends of the straps. In any event, the function of the straps is to releasably secure the sheet in encircling relationship to the extremity, as and after, the sheet is being or has been made to conform to the shape and size of the extremity. The number of straps employed to secure the sheet about the extremity is a function of the length dimension of the immobilizer (as measured along the length of the limb). Preferably, at least three straps are employed, ones 18, 22 adjacent each of the opposite ends 38, 39, respectively, of the immobilizer and a third strap 20 located approximately midway between the end straps. This number of straps and their relative locations on the immobilizer serve to intersect the reinforcing and stabilizing wire members that are oriented with the length of the immobilizer at locations that are spaced sufficiently close together as will enhance the resistance of the wire members to bend, by shortening the effective length of a wire member between adjacent straps.

With reference to FIGS. 2 and 3, the sheet of material which forms the body 40 of the immobilizer is initially substantially planar. It is provided with a plurality of openings, such as openings 42, 44, 46, 48, and 50 through the thickness thereof and at spaced apart locations over the area of the sheet. As noted hereinabove, these openings serve various and diverse functions. Each of the openings, except opening 50, preferably is of an elongated geometry, e.g. a slot, but other opening geometries may be used. In particular, the openings 42, 44 and 46, 48 are specially designed to aid in the application of the immobilizer to the extremity. Specifically, each of these openings 42, 44 and 46, 48 is of a size sufficient to receive therein the tips of the fingers or thumbs of a medical worker for purposes which will be discussed more fully hereinafter. The depicted openings 52 (typical) are also of elongated geometry and serve as ports through which air may flow to enhance the cooling and aeration of the space between the immobilizer and the limb.

As depicted in FIGS. 2 and 3, the sheet 16 of foam material has embedded therein a system of wire-like reinforcing and stabilizing members 54, 56, 58, 60, 62 and 64. This system may comprise a plurality of individual wire members, or a continuous wire member which is formed into a pattern having a plurality of runs. In the embodiment depicted in FIGS. 2 and 3, the members 54,56,62 and 64 are relatively straight individual members, whereas members 58 and 58' are initially contoured mirror images of one another with their abutting ends 65,68 and 66,70 being connected as by means of sleeves 72 and 74. On the other hand, the member 60 in the depicted embodiment is of a continuous length, but is formed into a generally "Y" configuration with its ends 76 and 78 abutting and connected as by a sleeve 80. In any event, there is provided reinforcement and stabilization to the immobilizer in selected areas thereof. The selection and placement of these member (or runs) within the sheet is a function of the intended final shape of the immobilizer and of the area of a limb which is to be immobilized, for example a wrist wherein provision must be made for thumb encirclement. In the embodiment depicted in FIG. 1, the immobilizer 10 is shown as being placed on a wrist. In this embodiment, it is desired that the wrist be immobilized so that reinforcing and stabilizing members 54, 56, 58, 60, 62, and 64 are located in spaced apart locations such that when the sheet is placed in encircling relationship to the wrist, these members extend along and generally parallel to the length of the extremity. In a preferred wrist immobilizer, the sheet includes an opening 50 through the thickness of the sheet through which the thumb 84 of the patient is received. In this embodiment, the members 58 and 60 include sections 58" and 60' thereof which extend about the circumference of the opening 50 in a manner such that when the immobilizer is in position on the wrist, these sections 58" and 60' provide reinforcement and stabilization to that portion 82 of the sheet which encircles the thumb and overlies the dorsal and ventral areas of the thumb and its Thenar eminence. Other sections 86,86' and 88,88' of the members 58 and 60, respectively, provide reinforcement and stabilization of the ends 38 and 39 of the immobilizer.

In accordance with one aspect of the present invention, each of the wire members is fully embedded within the foam sheet so that there is a substantial thickness of cushioning foam between the member and the skin of the patient and between each of the members and the outer surface of the immobilizer. This cushioning foam permits the medical worker to apply force to the sheet and its embedded, relatively stiff, wire members sufficient to bend (recontour) the wire members in selected regions to cause the sheet to conform to the shape and size of the encircled portion of the limb, without there being localized, and painful, pressure exerted against the limb and without the relatively small diameter wire painfully cutting into the hands of the medical worker or the limb of the patient. For example, this arrangement permits contouring of the immobilizer merely by the medical worker wrapping his hands about the immobilizer in a given location along the length of the immobilizer while it is positioned about the limb, and, by squeezing upon the immobilizer with his hands, applying pressure to the immobilizer sufficient to bend the wire members into close conformity with the shape and size of the limb in only that area which is encircled by the hands. By repeating this squeezing procedure to apply circumferential pressure to the immobilizer at any of many locations along the length of the immobilizer, the immobilizer may be caused to very closely conform to the shape and size of the limb underlying the immobilizer along substantially the full length of the immobilizer, all without undue pain to either the patient or the medical worker. Preferably this contouring of the immobilizer to the limb while the strapping thereof is relatively loose so that the sheet is free to "move" in response to the applied pressure. However, after the strapping has been pulled tight and its free ends anchored, further contouring of the immobilizer is possible, but to a lesser degree than when the strapping is relatively loose, but sufficiently tight as causes the strapping to hold the sheet in encircling relationship to the limb in the desired location on the limb.

In one embodiment of the present invention, the sheet material preferably is a polyethylene foam, but other types of foam can also be used such as, for example, polypropylene foam, ionomer foam, polystyrene foam, polyruethane foam, polyvinylchloride flexible foam and silicone foam. Preferably the foam is of the closed cell type. Again preferably, the foam sheet initially comprises first and second layers 91 and 93, the first layer being formed and overlaid with the system of wire members, and the second layer being overlaid upon the first layer with the system of wire members disposed between the first and second layers. These layers of foam, with the system of wire members disposed therebetween are bonded to one another (and to the wire members themselves in some instances) to form a unitary sheet. Bonding of the layers of foam may be by heat or, in some instances, by means of an adhesive. Among the advantages of the polyethylene foam are its desirable characteristics of low water absorption, good energy absorption, water vapor barrier, compressibility, smooth outer surface, thermal stability at temperatures up to about 215 degrees F. and a high ratio of tensile and shear strength to weight compared to other resilient foams. In addition, the capability of being heat sealed also makes it attractive.

Further, in a preferred embodiment, that surface 94 (See FIGS. 3 and 4) of the foam sheet which is intended to be nearest the limb when the immobilizer is applied, is covered with a further layer of soft, pliable foam 96. The outermost surface of this layer 96 of foam is covered by a layer 98 of fibrous material, preferably a hydrophilic fiber such as cotton or polyester. In one embodiment, the layer 96 is of an open-cell foam so that liquid wicked by the fibrous material from the patient's skin underneath the immobilizer is absorbed in the foam layer 96, thereby aiding in keeping the skin under the immobilizer free of deleterious moisture. This absorbed moisture is free to evaporate from the exposed side margins of the foam layer 96 to further enhance the drying effect.

The wire members of the reinforcing and stabilization system of the present invention preferably are of aluminum or an aluminum alloy. A wire diameter of about one-eighth inch has been found suitable, but other wire diameters are permissible so long as the wire member is bendable by hand. As noted, the wire members are each fully embedded within the foam sheet. In one embodiment, the system of wire members may be formed from a single length of wire which is bent into a pattern that provides reinforcement and stabilization of the immobilizer in selected strategic locations spaced over the area of the sheet. In another embodiment the system of wire members may be formed from several individual lengths of wire. In this latter embodiment, any abutting ends of the individual lengths of wires may be joined as by duct tape or other connector such as a plastic sleeve, for example. Metal connectors also may be used or, if desired, the abutting wire ends may be soldered or welded to one another. Whereas it is preferred that the reinforcing and stabilizing members of the present immobilizer be wire, i.e. of a circular cross section, it is intended that the term "wire" include therein elongated reinforcing and stabilizing members which may have a cross section that is other than circular, e.g. oblong. Circular cross sectioned members are preferred because they are amenable to being bent (contoured) omnidirectionally about their longitudinal axis.

This feature imparts to the present immobilizer the ability to more readily shape the immobilizer to enhance its conformity to the contour and size of a limb.

In a typical immobilizer, in accordance with the present invention, for a common wrist, the foam sheet of the immobilizer may be of a length of about nine inches between its ends 38 and 39, and of a width between its opposite side edges 41 and 43 that increases from about 9.5 inches at its end 38 to about 10.5 inches at its opposite end 39. Obviously, other size foam sheets may be employed for larger or smaller limbs.

In the depicted embodiment, the wire members 54,56,60 and 62 are disposed generally parallel with the length of the immobilizer, hence the length of an underlying limb when the immobilizer is applied to the limb. Likewise, the wire members 58 and 60, each include major sections 84,84' and 86,86', respectively, which extend longitudinally of the immobilizer. In this embodiment, this alignment of the wire members provides four longitudinally-aligned wire members (or major sections thereof) disposed on opposite sides of the longitudinal centerline 90 of the foam sheet 16 as seen in FIGS. 2 and 3. Notably, when the immobilizer depicted in FIG. 2 is positioned in encircling relationship about the right-hand wrist of a limb, the wire members 56 and 62 are aligned with the longitudinal centerline of the limb and centrally on the ventral and dorsal sides, respectively, of the limb. This positioning of the members 56 and 62 further positions the wire member 54 on the ventral side of the limb and along the medial side of the limb, and the wire member 64 on the dorsal side of the limb and also along the medial side of the limb. The major sections 84 and 84' of the member 58 consequently are positioned along the ventral and dorsal sides of the limb, respectively, and lie generally along the ventral lateral and dorsal lateral sides, respectively, of the limb. Likewise, the major sections 86 and 86' are positioned along the ventral and dorsal sides of the limb and also lie generally along the lateral side of the limb. When unbound by the straps 18,20 and 22, the overall effective length of each member is relatively long so that each member is readily bendable omnidirectionally about its longitudinal centerline to cause the member to conform to the contour and size of the underlying limb. This bending and contouring of the several wire members most readily takes the form of a bending of each member along its length. Some lateral bending of the members is also possible, however, as needed. Once the members have been recontoured to the contour of the underlying limb and the straps have been tightened, the effective length of each member is divided into two sections, a section being disposed between adjacent ones of the straps. By this means, the resistance to further bending of each wire member is greatly increased such that these members, when bound in good conforming relationship to the underlying limb, effectively immobilize the underlying limb.

In wrist immobilizers, it is common that the thumb be exposed outside the immobilizer (i.e. non-abducted) and free to be moved. This situation is accommodated in the present invention by means of the opening 50. However, it is further desired that this movement of the thumb not be allowed to interfere or reduce the desired immobilization of the wrist. Therefore, in accordance with the present invention, the wire members 58 and 60 are provided with sections 58" and 60' which encircle the Tenier eminence of the thumb when the thumb projects through the opening 50. These sections are initially contoured to accept the Tenier eminence, but may be recontoured to ensure comfortable conformity with the Tenar eminence. If required, or desired, the foam sheet may be cut away to expand the circumference of the opening 50, and in like manner, the sections 58" and 60' of the wire members 58 and 60 also may be cut away in this area to relieve any undue pressure against the thumb.

In accordance with a further aspect of the invention, it has been found that once the immobilizer has been initially fitted to the limb, the present immobilizer may be readily removed and replaced by the patient without the aid of a third party. This feature is particularly useful when the immobilizer is used to immobilize the wrist. More specifically, the initial contouring of the immobilizer to the limb imparts a substantial degree of shape to the immobilizer. This degree of shape is retained even when the immobilizer is removed from the limb. Further, this degree of shape is sufficient to permit a patient to place the immobilizer about the injured wrist, rest the limb and immobilizer on a table or the like, and feed the several straps through their respective rings or buckles. Thereupon, initial tightening of the straps can be employed to bring the immobilizer into its conforming relationship to the limb. As needed, with their free hand, the patient can urge the sheet into enhanced conformity with the limb and thereupon further tighten the strapping to secure the immobilizer to the limb.

Whereas the immobilizer of the present invention has been described primarily in terms of a wrist immobilizer, it will be recognized by one skilled in the art that the concepts of the present invention may be transferred readily to the construction of an ankle immobilizer.

What is claimed:

1. An immobilizer for a limb comprising a body member of generally rectangular planar geometry, having a longitudinal centerline, first and second side edges on opposite sides of said longitudinal centerline, outer and inner surfaces, and which is amenable to ready conformance with the shape and size of a limb when in encircling relationship with the limb and covering a region of the limb to be immobilized, said body member including at least one layer of a soft pliable foam material of a size and shape sufficient to encircle the region of the limb to be immobilized, a system of reinforcing and stabilizing wire members substantially embedded within said layer of foam material, said system of wire members including a plurality of lengths of said wire members oriented generally parallel with said longitudinal centerline of said body member, a first portion of said wire members being disposed on one side of said longitudinal centerline and a further portion of said wire members being disposed on the opposite side of said longitudinal centerline, whereby when said body member is positioned in encircling relationship to a limb, said first and further portions of said wire members are aligned with the longitudinal centerline of the limb and on opposite sides of the limb and the opposite sides edges of said body member are disposed in juxtapositional relationship to one another means defining first and second openings through the thickness of said body member, said first opening being disposed adjacent one side edge of said body member and suitable to receive therein a thumb or finger, said second opening being disposed adjacent the opposite side edge of said body member and suitable to receive therein a thumb or finger, a plurality of strap means having respective opposite ends, one of the ends of each of said strap means being anchored to the outer surface of said body member with the free ends of each of said strap means being adapted to encircle said body member when the body member is disposed in encircling relationship to the limb, and means releasably securing said free ends of said strap means when said strap means encircle said body member.

2. The immobilizer of claim 1 wherein at least one of said wire members extends along one of the side edges of said body member and is spaced between said opening associated with the side edge and the side edge itself.

3. The immobilizer of claim 1 and including further openings through the thickness of said body member.

4. The immobilizer of claim 3 wherein said further openings include third and fourth openings disposed adjacent respective ones of the opposite side edges of said body member, each of said third and fourth openings being adapted to receive therein a thumb or finger.

5. The immobilizer of claim 1 wherein said body member includes first and second layers of foam material and said wire members are disposed between said layers.

6. The immobilizer of claim 1 and including a layer of soft pliable foam bonded to the inner surface of said body member, and a hydrophilic fibrous covering on the exposed surface of said layer of soft pliable foam in position to contact the limb when said body member is positioned in encircling relationship to the limb.

7. The immobilizer of claim 1 wherein each of said wire members is sufficient malleable to render it amenable to bending about its length dimension by hand.

8. The immobilizer of claim 1 wherein said straps intersect said wire members when said body member is in encircling relationship to the limb and said straps are encircled about said body member.

9. The immobilizer of claim 8 wherein said straps are spaced apart from one another member length of said body member whereby tightening of said straps serves to divide said wire members into effective lengths that are shorter than the respective overall lengths of the wire members.

10. The body member of claim 1 and including a further layer of soft foam material bonded to one surface of said body member, said layer of soft foam material including a covering of hydrophilic fibers on that surface thereof which is nonbonded.

11. A body member of generally rectangular planar geometry and suitable for use in a limb immobilizer comprising a layer of a soft foam material of a size and shape sufficient to encircle a region of the limb to be immobilized and having first and second side edges, a system of reinforcing and stabilizing wire members embedded within said layer of foam material and including runs thereof that are spaced apart from one another and at spaced locations over the area of the body member whereby when said body member is disposed in encircling relationship to the limb to be immobilized, a first portion of said wire members are disposed on one side of the limb and a further portion of said wire members are disposed on the opposite side of the limb with the side edges of said body member being in juxtapositional relationship to one another, said wire members being sufficiently malleable as to render the same amenable to bending by hand about their respective length dimension, a first one of said runs being disposed adjacent to and inwardly of one side edge of said body member and being oriented generally parallel to said one side edge, a second one of said runs being disposed adjacent to and inwardly of that side edge opposite said one side edge of said body member and being oriented generally parallel to said opposite side edge, means defining a plurality of openings through the thickness of said body member, at least first and second ones of said openings being disposed adjacent the opposite side edges of said body member and inwardly of respective ones of said first and second runs of said wire members, and a plurality of strap means adapted to encircle said body member when the same is disposed in encircling relationship to the limb and secure said body member in conforming relationship to the limb.

12. The body member of claim 11 wherein said body member includes first and second layers of foam material overlaid one upon the other and bonded to one another at their interface and said system of wire members is disposed between said first and second layers of foam material.

13. The body member of claim 11 wherein each of said first and second openings is adapted to receive therein a thumb or finger.

* * * * *